(12) United States Patent
Sato (10) Patent No.: US 7,837,618 B2
(45) Date of Patent: Nov. 23, 2010

(54) ENDOSCOPE CONTROL SYSTEM

(75) Inventor: Saichi Sato, Sagamihara (JP)

(73) Assignee: Olympus Corporation, Tokyo (JP)

( * ) Notice: Subject to any disclaimer, the term of this patent is extended or adjusted under 35 U.S.C. 154(b) by 663 days.

(21) Appl. No.: 11/284,062

(22) Filed: Nov. 21, 2005

(65) Prior Publication Data

US 2006/0142641 A1     Jun. 29, 2006

(30) Foreign Application Priority Data

Nov. 24, 2004   (JP) .............................. 2004-338799

(51) Int. Cl.
*A61B 1/04* (2006.01)
(52) U.S. Cl. ...................... 600/118; 600/109; 358/1.15
(58) Field of Classification Search ................. 600/109, 600/117, 118; 348/65, 68, 69, 73, 74
See application file for complete search history.

(56) References Cited

U.S. PATENT DOCUMENTS

| 6,602,185 | B1 * | 8/2003 | Uchikubo | 600/118 |
| 7,299,359 | B2 * | 11/2007 | Hurley | 713/182 |
| 7,515,289 | B2 * | 4/2009 | Ohtuka | 358/1.15 |
| 2002/0101619 | A1 * | 8/2002 | Tsubaki et al. | 358/302 |
| 2003/0122881 | A1 * | 7/2003 | Yoshida | 345/862 |
| 2003/0123696 | A1 * | 7/2003 | Matsumoto et al. | 382/100 |
| 2003/0128400 | A1 * | 7/2003 | Watai et al. | 358/296 |
| 2004/0054775 | A1 * | 3/2004 | Poliac et al. | 709/224 |
| 2004/0183830 | A1 * | 9/2004 | Cody et al. | 345/752 |
| 2004/0225185 | A1 * | 11/2004 | Obata et al. | 600/118 |
| 2005/0094189 | A1 * | 5/2005 | Aoyama et al. | 358/1.15 |
| 2005/0257159 | A1 * | 11/2005 | Keohane et al. | 715/752 |

FOREIGN PATENT DOCUMENTS

JP     2003-135371     5/2003

* cited by examiner

*Primary Examiner*—John P Leubecker
*Assistant Examiner*—Samuel Candler
(74) *Attorney, Agent, or Firm*—Scully, Scott, Murphy & Presser, P.C.

(57) ABSTRACT

In an endoscope control system, endoscope devices capture an image of each inspection site, write endoscope information in a title and/or a text of an electronic mail, and transmit the captured image in the electronic mail which has a captured image management computer of a management center as its distribution destination. The captured image management computer of the management center receives the captured images from the endoscope devices in the electronic mails, and manages them collectively.

18 Claims, 7 Drawing Sheets

ENDOSCOPE CONTROL SYSTEM

BACKGROUND OF THE INVENTION

Priority is claimed on Japanese Patent Application No. 2004-338799, filed Nov. 24, 2004, the content of which is incorporated herein by reference.

FIELD OF THE INVENTION

The present invention relates to an endoscope control system that is suitable for use when a monitoring center collectively monitors captured images which are captured by endoscopes at inspection regions of inspection sites.

DESCRIPTION OF RELATED ART

Endoscope devices are widely used in medical and industrial fields. As for example described in Japanese Unexamined Patent Application, First Publication, No. 2003-135371, an endoscope has an elongated insertion unit that can be inserted into an inspection region, and is inserted into piping of a body cavity, an engine, an industrial plant, and such like, where it observes the target region. An image-capturing unit such as a charge coupled device (CCD) is provided at a tip of the insertion unit of the endoscope device, and an image captured thereby is displayed as an observation image on a display unit such as a monitor. Such endoscope devices are equipped with a control switch or the like which, when turned on, causes the captured image to be recorded onto a recording medium inside the endoscope device or a recording medium which can be connected to the endoscope device.

Conventionally, to manage the image captured by the endoscope, an operator of the endoscope transfers the captured image recorded in the recording medium to a personal computer or the like. At this time, when there is endoscope information such as the date when the image was captured, the title of the image, the correction value of the image-capturing lens, the lens type, the management number of the endoscope device, and captured image correction information, the endoscope operator inputs this endoscope information and attaches them to image files and the like.

In industrial fields, endoscopes may be used in a plurality of workplaces, such as in airplane engine maintenance of various locations and in piping maintenance of vast industrial plants, and the images they capture are collectively managed by a central computer such as a management center. In this case, the recording medium is removed from the endoscope after work is completed. The recording medium is connected to a computer of the operator and the captured image in the recording medium is transferred to this computer. The operator confirms the captured image, conditions, and so on, creates and appends data, and transmits the captured image by electronic mail to a captured image manager at the management center. When the captured image is recorded in a built-in recording medium of the endoscope, the endoscope is connected to the computer and the captured image is transferred to the computer via a communication. By means of the computer, the operator confirms the image, conditions, and so on, creates and appends data, and transmits the captured image with the appended data by electronic mail to the captured image manager at the management center.

SUMMARY OF THE INVENTION

An endoscope control system according to the present invention comprises a captured image management device which collectively manages captured images which are transmitted thereto via a network on a predetermined communication system, and an endoscope device including an image-capturing unit which captures an image of an inspection region and a transmitter which transmits the captured image captured by the image-capturing unit via the network on the predetermined communication system to the captured image management device.

In the endoscope control system according to this invention, the communication system may be an electronic mail communication system, the captured image management device may collectively manage the captured image transmitted by electronic mail via the network, the endoscope device may include a mail creation unit which creates an electronic mail destined for the captured image management device with the captured image captured by the image-capturing unit attached thereto, and the transmitter may transmit the created electronic mail to the network.

Further, in the endoscope control system according to this invention, the endoscope device may include a device control unit and a distribution controller which distributes the captured image to the communication system when a control signal from the device control unit is input.

Further, in the endoscope control system according to this invention, the endoscope device may be connected to a long-distance control unit and may include a distribution controller which distributes the captured image via the communication system or the electronic mail when a control signal from the long-distance control unit is input.

Furthermore, in the endoscope control system according to this invention, the endoscope device may include a timer and a distribution controller which distributes the captured image via the communication system or the electronic mail when the timer reaches a desired date and time.

Still further, in the endoscope control system according to this invention, an external trigger signal may be supplied to the endoscope device, and the endoscope device may include a distribution controller which distributes the captured image via the communication system or the electronic mail when the external trigger signal is input.

Furthermore, in the endoscope control system according to this invention, the endoscope device may include an endoscope information storage unit which stores endoscope information.

Yet further, in the endoscope control system according to this invention, the endoscope information may include at least the date and time when the image was captured, the title of the captured image, the correction value of the image-capturing lens, the lens type, the management number of the endoscope device, captured image correction information, and user information.

Further, in the endoscope control system according to this invention, the endoscope device may include an endoscope information storage unit which stores the endoscope information, and the mail creation unit may store the captured image together with the endoscope information stored in the endoscope information storage unit.

Furthermore, in the endoscope control system according to this invention, the mail creation unit may write the endoscope information in the title and/or a text of the electronic mail.

DETAILED DESCRIPTION OF THE INVENTION

An embodiment of the present invention will be explained in detail with reference to the drawings.

Figure 1:
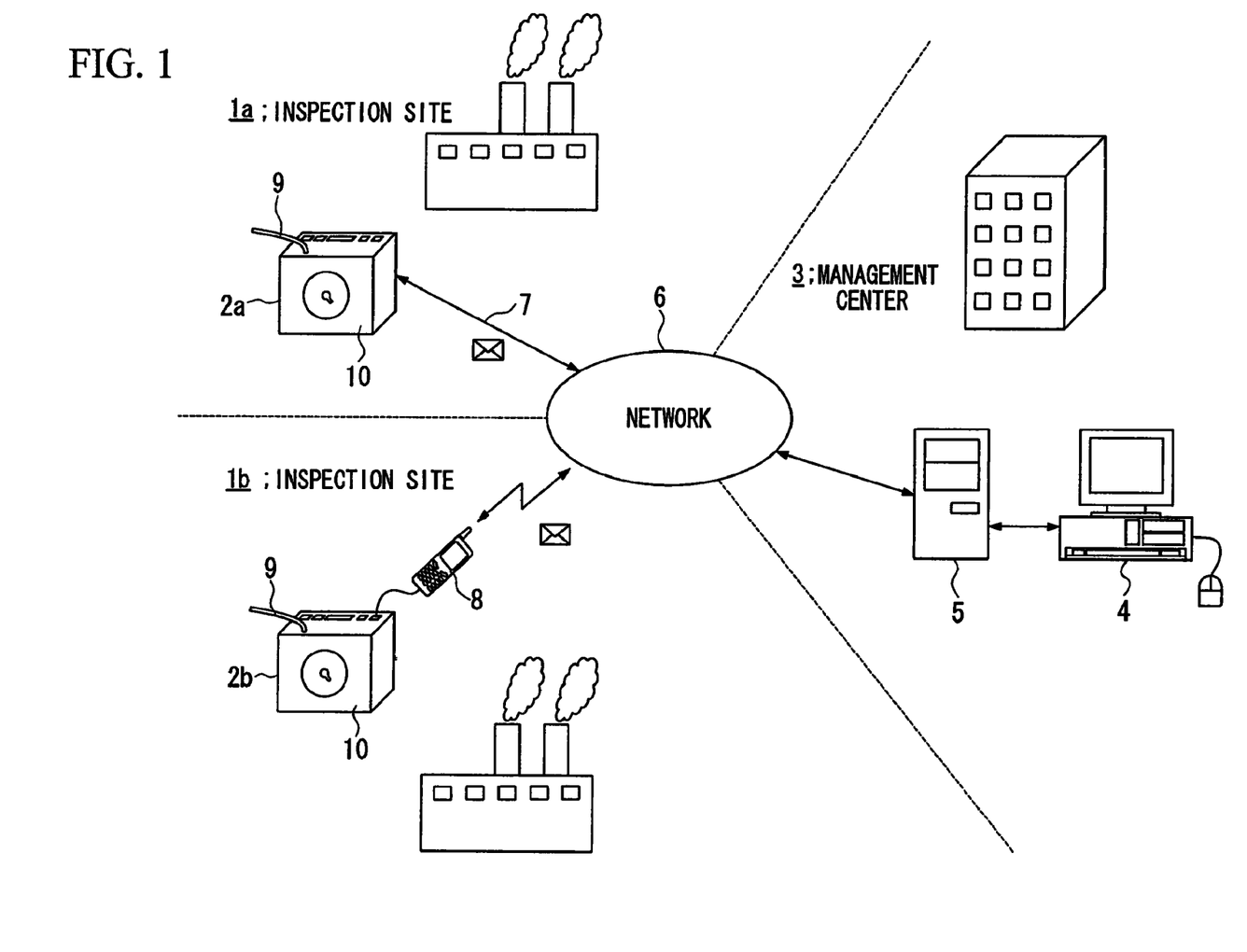
FIG. 1 is a schematic view showing the overall configuration of an endoscope control system according to an embodiment of the present invention.

FIG. 1 is a diagram showing the overall configuration of an endoscope control system according to an embodiment of the present invention. In FIG. 1, endoscope devices 2a and 2b are arranged at inspection sites 1a and 1b, and are used in taking images of regions inside the inspection sites 1a and 1b. For example, when used in an industrial field, the inspection sites 1a and 1b are sites where work is carried out, e.g. airplane engine maintenance or piping maintenance of a vast industrial plant. While there are two inspection sites 1a and 1b in this example, the number of inspection sites is not limited to two. Also, while one of the endoscope devices 2a and 2b is arranged at each of the inspection sites 1a and 1b in this example, the number of endoscope devices arranged at the inspection sites 1a and 1b is not limited to this.

Figure 2:
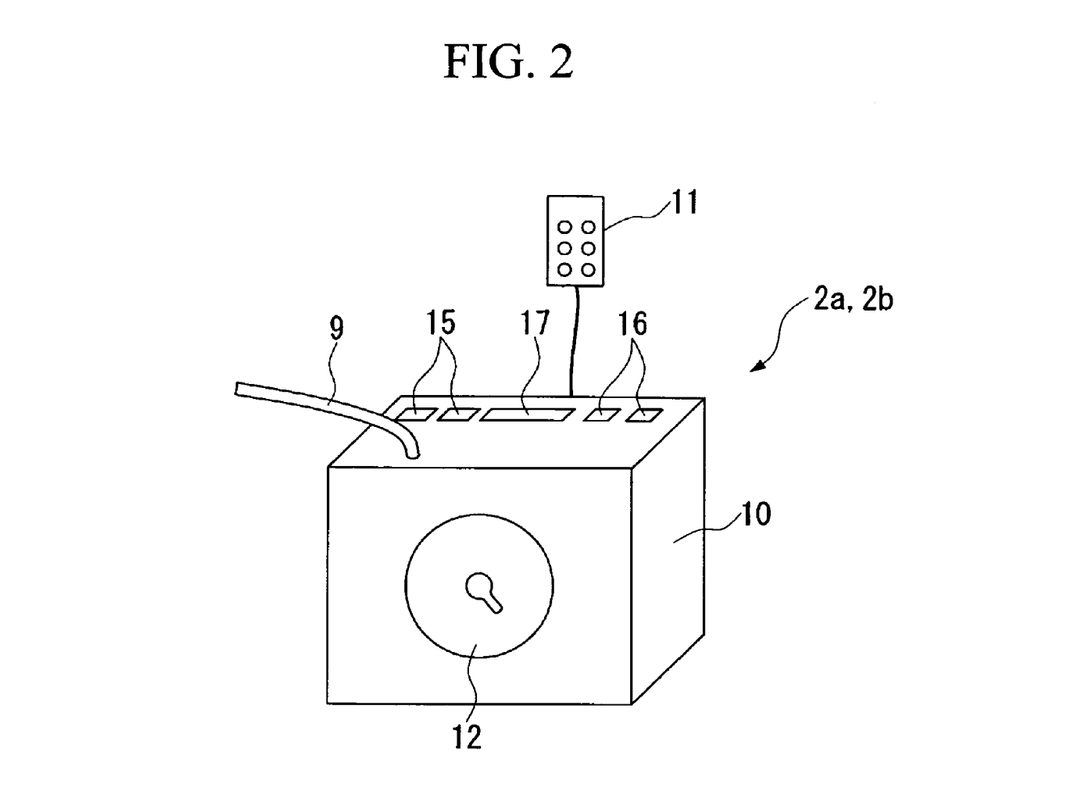
FIG. 2 is a perspective view showing the exterior of an endoscope device according to the embodiment of the present invention.
Figure 3:
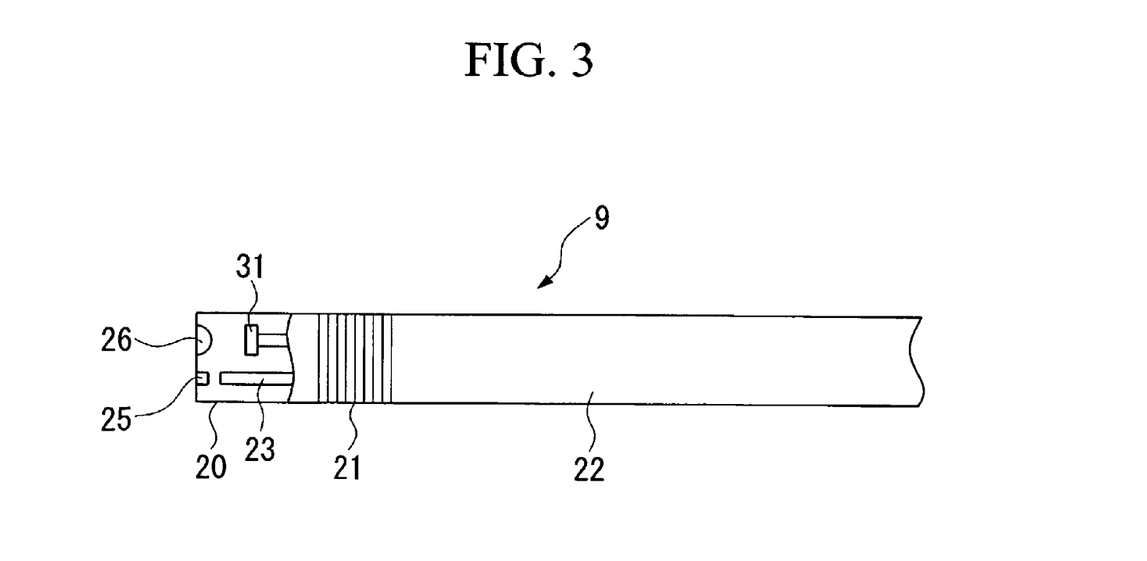
FIG. 3 is a side view showing an insertion unit of the endoscope device according to the embodiment of the present invention.

The endoscope devices 2a and 2b capture images of internal inspection regions. As shown in FIG. 2b, each of the endoscope devices 2a and 2b has an elongated insertion unit 9 which can be inserted into an inspection region, and, as shown in FIG. 3, a CCD 31 is provided at the tip of the insertion unit 9. The tip of the insertion unit 9 can be freely bent, enabling endoscope images to be captured over a wide area. Incidentally, the endoscope devices 2a and 2b are not limited to this configuration. The endoscope devices 2a and 2b include a function for transmitting electronic mails via a network 6.

A management center 3 is located at a distance from the inspection sites 1a and 1b, and manages the endoscope images of the inspection sites 1a and 1b that are captured by the endoscope devices 2a and 2b. A captured image management computer 4 is provided at the management center 3. The captured image management computer 4 includes at least a function for managing and displaying images, and a function for transmitting and receiving electronic mails by connecting to the network 6. Images captured by the endoscope devices 2a and 2b at the inspection sites 1a and 1b are transmitted by electronic mail to the captured image management computer 4 at the management center 3. At the management center 3, the endoscope images captured by the endoscope devices 2a and 2b at the inspection sites 1a and 1b are managed using the captured image management computer 4.

The network 6 exchanges data between the endoscope devices 2a and 2b of the inspection sites 1a and 1b, the captured image management computer 4, and a mail server 5. The network 6 is, for example, the internet. In addition to a computer network, the network 6 may include a public telephone line, a mobile telephone line, a wired or wireless local area network (LAN), and such like. With regard to the format for connecting of the endoscope devices 2a and 2b of the inspection sites 1a and 1b, the captured image management computer 4, the mail server 5, and the network 6, it is acceptable to use any connection format which can transmit/receive electronic mails.

In this embodiment shown in FIG. 1, the endoscope device 2a in the inspection site 1a is directly connected to the network 6 by a cable 7. The endoscope device 2b in the inspection site 1b is connected to the network 6 via a portable terminal 8.

The mail server 5 is provided to the network 6. The mail server 5 transfers mails between all apparatuses which connect to the network 6. A simple mail transfer protocol (SMTP) and a post office protocol (POP) are, for example, used in transferring or relaying mails. An electronic mail transmitting/receiving program is installed in the endoscope devices 2a and 2b and the captured image management computer 4, and supports these SMTP and POP mail transfer protocols. The mail relay protocols are not limited to those described here. The mails may also be encrypted.

In the endoscope control system of this embodiment, the endoscope images captured by the endoscope devices 2a and 2b at the inspection sites 1a and 1b are distributed to the captured image management computer 4 of the management center 3 by transmitting electronic mails from the endoscope devices 2a and 2b via the network 6. The endoscope images from the endoscope devices 2a and 2b of the inspection sites 1a and 1b are relayed via the network 6 and temporarily accumulated in the mail server 5 before being received by the captured image management computer 4 of the management center 3.

The electronic mails of the images captured by the endoscope devices 2a and 2b are transmitted when an operator of the endoscope makes an input operation to a control unit and a long-distance control unit, the electronic mails being transmitted when a timer reaches a desired date and time. The images are also transmitted by electronic mail when a trigger signal is input from the outside. When there is endoscope information such as the date and time when the image was captured, the title of the captured image, the lens type, the correction value of the image-capturing lens, the management number of the endoscope device, captured image correction information, and user information, this endoscope information is written in the title and/or the text of the electronic mail and transmitted by electronic mail together with the endoscope image. The user information included in the endoscope information is information which enables the inspector to be identified, such as the name of the inspector, an identification (ID) number of the inspector, etc.

Thus in the endoscope control system which the present invention is applied in, the endoscope images captured by the endoscope devices 2a and 2b of the inspection sites 1a and 1b are transmitted directly to the captured image management computer 4 of the management center 3 by electronic mail. An operator at the management center 3 can look at images which are sent to him by electronic mail and work on them in that state. There is consequently no need to perform operations such as transferring the images from a recording medium of the endoscope to the operator's computer.

The electronic mail consists of information which is arranged and transmitted as a title, a text, and an attached file. The transmission/reception date and time of the electronic mail can be managed. By using this feature effectively, the endoscope images transmitted from the endoscope devices 2a and 2b of the inspection sites 1a and 1b can be managed efficiently. This avoids placing a burden on the image manager and greatly alleviates the post-inspection burden on the operator and the image manager. By transmitting the endoscope images from the endoscope devices 2a and 2b of the examination sites 1a and 1b directly to the captured image management computer 4 of the management center 3, the observation image can be corrected and prevented from falsification. Moreover, writing the user information in the electronic mail makes it easier to manage the inspection history.

Subsequently, the endoscope devices 2a and 2b of this embodiment will be explained. In FIG. 2, the long insertion unit 9 of the endoscope devices 2a and 2b is reeled by a rotatable drum 12 and stored in a device casing 10. A power switch, various types of control switches 15, various types of connectors 16 which connect to a cable and a mobile telephone which connect to the network 6, and a slot for memory card 17 for attaching/removing a detachable recording medium such as a memory card, are provided on the top face of the device casing 10.

As shown in FIG. 3, the insertion unit 9 includes a hard tip section 20 provided at the tip, a freely bendable bending section 21 provided at a rear end of the tip section 20, and a flexible section 22 provided at a rear end of the bending section 21. A light guide 23 that transmits illuminating light is inserted into the insertion unit 9, and its rear end is connected to a light source (not shown) which has a built-in lamp. Light generated by this lamp is incident upon a side face of the light guide 23, and is transmitted by the light guide 23 to a side face on the tip side.

The light from the light guide 23 is emitted forwards from the tip face via an illuminating lens 25, and illuminates a target. An observation window is provided adjacent to an illuminating window for illumination, and an image of the target is formed by an objective lens 26 which is attached to the observation window. An image-capturing element such as the CCD 31, which is provided at the image formation position, photoelectrically converts the image and leads it inside.

Figure 4:
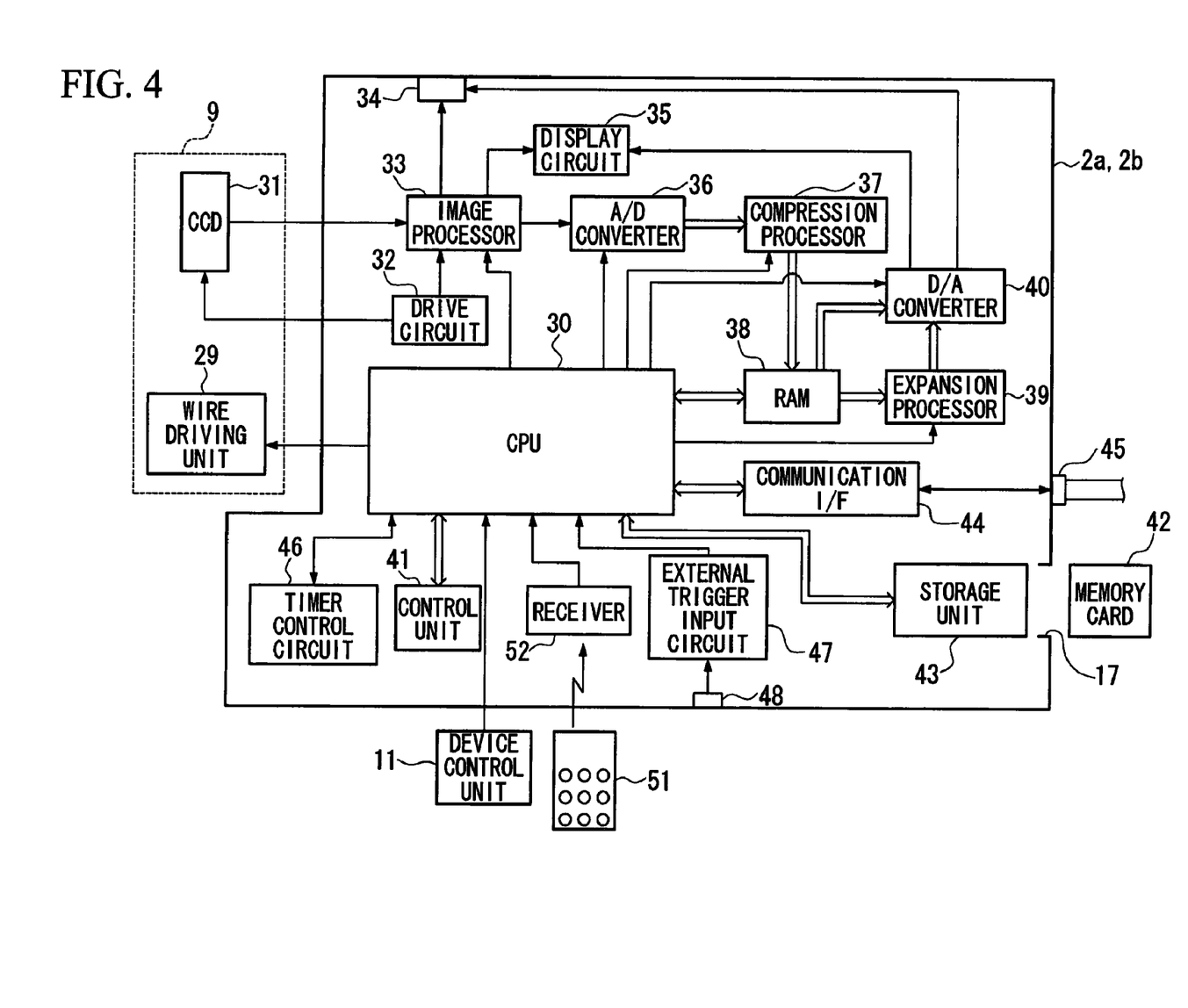
FIG. 4 is a block diagram showing the endoscope device according to the embodiment of the present invention.

FIG. 4 is a diagram of a block configuration for processing and transmitting an endoscope image in the endoscope devices 2a and 2b. While FIG. 4 depicts only constituent parts which are necessary to explain the present invention, it is assumed that other constituent parts and the like for executing normal functions are also included.

In FIG. 4, a drive circuit 32 drives the CCD 31 attached to the tip of the insertion unit 9, whereby a captured image (endoscope image) signal which is converted to an electric signal by the photoelectrical conversion is sequentially transmitted to an image processing circuit 33. The tip of the insertion unit 9 can be freely bent by operating a wire driving unit 29. In accordance with a timing from the drive circuit 32, the image processor 33 processes the captured image signal in various ways e.g. amplification and color separation. The image processor 33 outputs to an image external terminal 34 and a display circuit 35. The display circuit 35 displays the input captured image.

A central processing unit (CPU) 30 controls all the processes of the endoscope devices 2a and 2b. A device control unit 11 supplies input to the CPU 30. A long-distance control unit 51 is connected to a network for controlling the endoscope devices 2a and 2b by long-distance, and a signal from the long-distance control unit 51 is transmitted to the CPU 30 via a receiver 52.

A video signal from the CCD 31 is sent from the image processor 33 to an analog-to-digital (A/D) converter 36, where it is digitalized and sent as image data to a compression processor 37. The compression processor 37 compresses the captured image data using a compression method which is suitable for image data, e.g. variable-length encoding of an orthogonal transform such as a discrete cosine transform (DCT), and sequentially stores the compressed image data in a random access memory (RAM) 38.

The compression processor 37 can also output image data of a non-compressed image by a resetting of its parameters, and this non-compressed image data is also sequentially stored in the random access memory (RAM) 38. The image processor 33 adjusts and processes the image data as appropriate using various processes, e.g. brightness adjustment and trimming.

The compressed image stored in the RAM 38 can be expanded by an expansion processor 39 before being converted to an analog signal by a digital-to-analog (D/A) converter 40 and output to the image external terminal 34 and the display circuit 35. The non-compressed image stored in the RAM 38 is converted to an analog signal by the D/A converter 40, and sent to the image external terminal 34 and the display circuit 35.

The RAM 38 functions as an area for storing compressed image data, expanding programs in a read only memory (ROM) 41, and so on. The RAM 38 may also store endoscope information such as the date and time when the image was captured, the title of the captured image, the lens type, the correction value of the image-capturing lens, the management number of the endoscope device, captured image correction information, and user information, and/or image distribution information (electronic mail distribution destination information). The RAM 38 may be given a backup power source by connecting it to a battery so that, even if the main power of the RAM 38 is cut off, its contents are preserved.

The ROM 41 may comprise a Flash ROM or an Electrically Erasable and Programmable Read Only Memory (EEPROM). In addition to programs, the compressed data, endoscope information and/or image distribution destination information (electronic mail distribution destination information), and so on, may also be stored.

Each of the endoscope devices 2a and 2b includes a memory card interface (interface) unit 43 for recording image information which contains the image data on a memory card 42 or the like, enabling the image data to be recorded when appropriate onto the memory card 42 when it is inserted into the slot for memory card 17 provided in the device casing. Furthermore, endoscope information including the title of the image, the correction value of the image-capturing lens, the lens type, the management number of the endoscope device, captured image correction information, image distribution destination information (electronic mail distribution destination information), and user information, may be written to the memory card 42. When the memory card 42 is inserted, this endoscope information can be read and used in the endoscope.

The endoscope devices 2a and 2b each include a communication I/F 44. The communication I/F 44 connects the endoscope devices 2a and 2b to the network 6. A universal serial bus (USB), a universal asynchronous receiver/transmitter (UART), and such like, can be used as the communication I/F 44. A communication connector 45 is connected to the communication I/F 44.

Each of the endoscope devices 2a and 2b includes a timer control circuit 46 and an external trigger input circuit 47. The timer control circuit 46 is provided in order to distribute the image by electronic mail at the desired date and time. The external trigger input circuit 47 is provided in order to distribute the image by electronic mail in compliance with an external trigger signal. A trigger signal from a trigger signal input terminal 48 is input to the external trigger input circuit 47.

The commands below are examples of commands applied from the device control unit 11 and the long-distance control unit 51.

(a) Image Record Command: A command to record an endoscope image captured by the CCD 31 onto a recording medium.

(b) Captured image Transmission Command: A command to transmit an endoscope image captured by the CCD 31 via electronic mail.

(c) Image Adjustment Command: A command to execute various adjustments to an image, e.g. brightness adjustment, trimming, etc.

(d) Insertion Unit Drive Command: A command to bend the tip of the insertion unit 9.

(e) Menu Display Command: A command to display a menu for inputting the title of the image and the distribution destination of the electronic mail.

A title character signal and a distribution destination character signal of the captured image (electronic mail) are input from the device control unit 11 and the long-distance control unit 51.

At the desired date and time, the endoscope devices 2a and 2b can distribute their captured images by electronic mail. The captured images can also be distributed by electronic mail in accordance with the external trigger signals.

Figure 5:
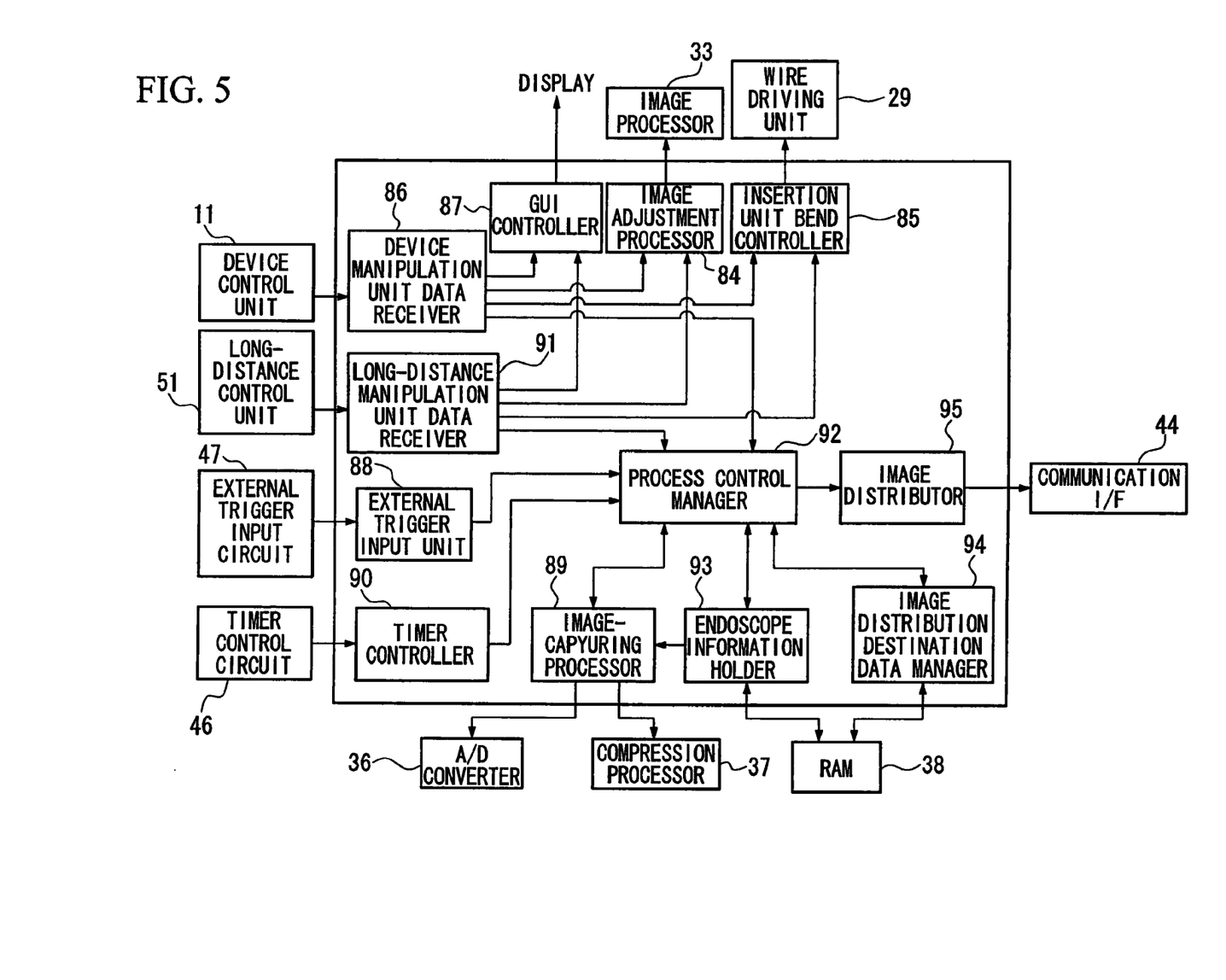
FIG. 5 is a block diagram showing functions of the endoscope device according to the embodiment of the present invention.

These operations will be explained more specifically with reference to the functional block diagram of FIG. 5.

The CPU 30 controls all the processes of the endoscope devices 2a and 2b. As shown in FIG. 5, when the functions realized by processes of the CPU 30 are arranged in blocks, they include an image adjustment processor 84, an insertion unit bend controller 85, a device control unit data receiver 86, a graphical user interface (GUI) controller 87, an external trigger input unit 88, an image-capturing processor 89, a timer controller 90, a long-distance control unit data receiver 91, a process control manager 92, an endoscope information holder 93, a captured image distribution destination data manager 94, and an image distributor 95.

The image adjustment processor 84 controls the image processor 33 so as to adjust the image quality and the like of an image, based on image adjustment processing data. The insertion unit bend controller 85 controls the wire driving unit 29 so as to bend the tip of the insertion unit 9, based on bend data. The device control unit data receiver 86 receives various types of command and characters from the device control unit 11, and transmits them to each unit. The GUI controller 87 executes a process to display a title input screen for the image and an image distribution destination input screen which forms the image (electronic mail) distribution destination.

When a digital or analog trigger signal is input to the external trigger input circuit 47, the external trigger input unit 88 executes a process in accordance with this trigger signal. The image-capturing processor 89 controls the A/D converter 36 and the compression processor 37 such as to execute processes of extracting, compressing, and decompressing the data processed by the image processor 33 which carries out image-processing to the image data captured by the CCD 31.

The timer controller 90 uses time information from the timer control circuit 46 to determine whether a set time has been reached. The long-distance control unit data receiver 91 receives various types of commands and characters from the long-distance control unit 51, and transmits them to each unit.

The process control manager 92 manages all the operations of each unit. The endoscope information holder 93 holds endoscope information such as the date and time when the image was captured, the title of the captured image, the lens type, the correction value of the image-capturing lens, the management number of the endoscope device, captured image correction information, and user information. The captured image distribution destination data manager 94 manages distribution destination data of electronic mails, such as the mail address of the transmission destination. The image distributor 95 creates electronic mail data, and transmits the created electronic mail via the communication I/F 44.

When an image record command is input to the device control unit 11 or the long-distance control unit 51, the device control unit data receiver 86 or the long-distance control unit data receiver 91 passes this image record command via the process control manager 92, and transmits an image obtain command to the image-capturing processor 89. When the image-capturing processor 89 receives the image obtain command, it controls the A/D converter 36 and the compression processor 37 such that the image data from the CCD 31 passes through the RAM 38 and the memory card I/F 43 and is stored in the memory card 42.

By such processes, when an image record command is input to the device control unit 11 or the long-distance control unit 51, the endoscope image captured by the CCD 31 is recorded on the memory card 42 which constitutes the recording medium. Incidentally, the selection between compressed image/non-compressed image may be made by a GUI.

When an image transmission command is input to the device control unit 11 or the long-distance control unit 51, the device control unit data receiver 86 or the long-distance control unit data receiver 91 transmits an image obtain command via the process control manager 92 to the image-capturing processor 89. When the image-capturing processor 89 receives the image obtain command, it controls the A/D converter 36 and the compression processor 37 such as to compress the image data from the CCD 31 and store it in the RAM 38. When storage of the compressed image in the RAM 38 is complete, the image-capturing processor 89 transmits a captured image storage completion notification to the process control manager 92.

When the process control manager 92 receives the captured image storage completion notification, it sends a distribution command relating to the image to the image distributor 95. When the image distributor 95 receives a distribution command relating to the image from the process control manager 92, it starts creating electronic mail data for the image.

Figure 6:
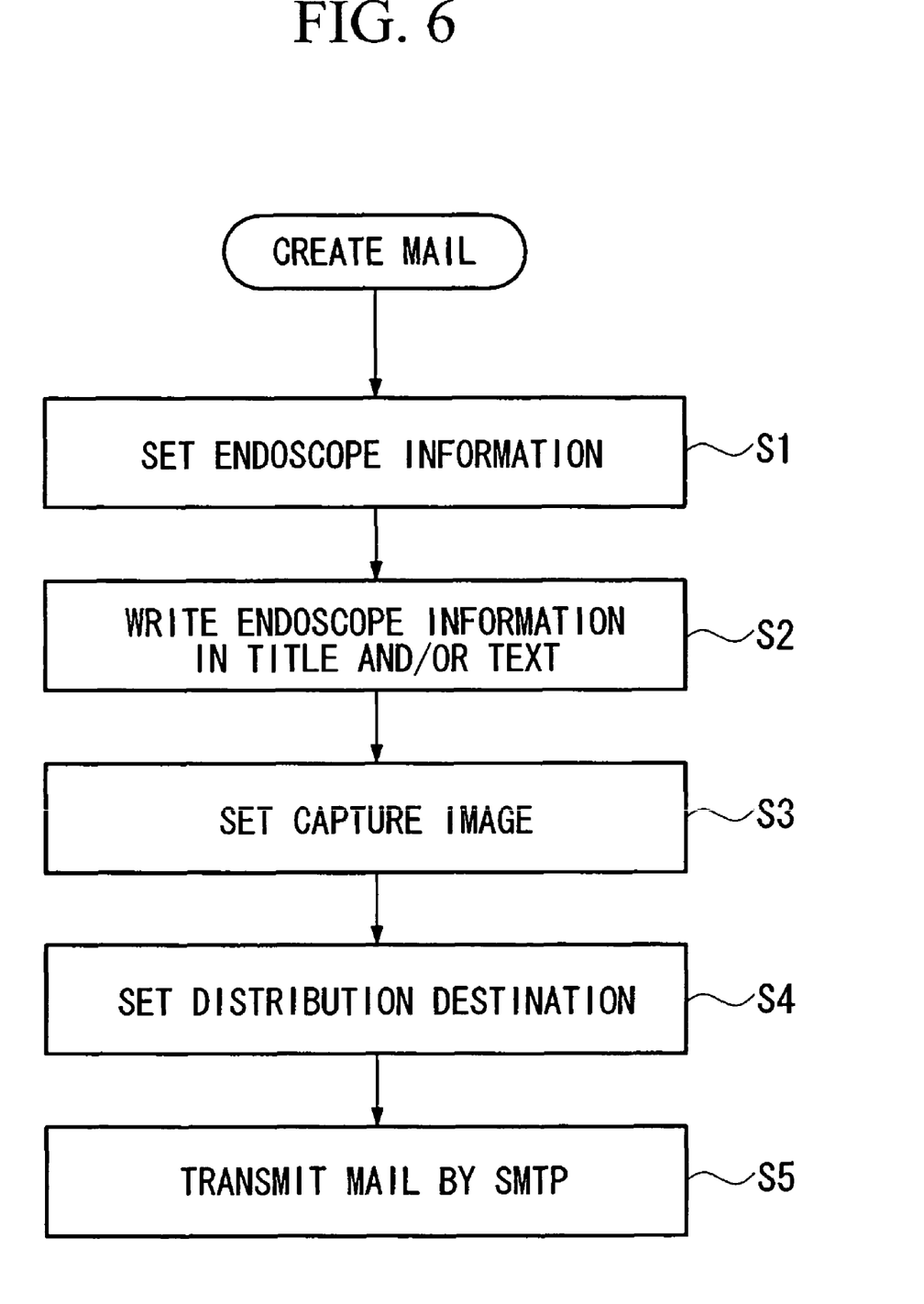
FIG. 6 is a flowchart showing an operation of the endoscope device according to the embodiment of the present invention.

As shown in FIG. 6, in this electronic mail creation process, the image distributor 95 reads the endoscope information from the endoscope information holder 93 (step S1) and writes this endoscope information in the title and/or text of the electronic mail (step S2). It then reads the image captured by the CCD 31 from the RAM 38, and attaches this image data to the electronic mail (step S3). The image distributor 95 reads the distribution destination data from the captured image distribution destination data manager 94 (step S4), creates image distribution destination (electronic mail distribution) data, and transmits the image data in an electronic mail according to a simple mail transfer protocol (SMTP) (step S5).

By such processes, when an image transmission command is input to the device control unit 11 or the long-distance control unit 51, the endoscope image captured by the CCD 31 is transmitted by electronic mail to the distribution destination. The selection between compressed image/non-compressed image may be made by a GUI.

When an image adjustment process command is input to the device control unit 11 or the long-distance control unit 51, the device control unit data receiver 86 or the long-distance control unit data receiver 91 receives various image adjustment process commands, such as brightness adjustment and trimming, from the device control unit 11 and the long-distance control unit 51, and transmits image adjustment process data to the image adjustment processor 84. When the image adjustment processor 84 receives this image adjustment process data, it controls the image processor 33 such as to adjust the image quality and the like of the image, based on the received image adjustment process data.

By such processes, when an image adjustment process command is input to the device control unit 11 or the long-distance control unit 51, the image is adjusted according to various processes such as brightness adjustment and trimming.

When an insertion unit bend command is input to the device control unit 11 or the long-distance control unit 51, the device control unit data receiver 86 receives a drive command for the insertion unit from the device control unit 11 or the long-distance control unit 51, and transmits bend control data for the insertion unit 9 to the insertion unit bend controller 85. When the insertion unit bend controller 85 receives this bend control data, it controls the wire driving unit 29 such as to bend the tip of the insertion unit 9, based on the received control data.

By such processes, when an insertion unit bend command is input to the device control unit 11 or the long-distance control unit 51, the tip of the insertion unit 9 is bent.

When a menu display command is input to the device control unit 11 or the long-distance control unit 51, the device control unit data receiver 86 or the long-distance control unit data receiver 91 transmits a menu display command to the GUI controller 87. When the GUI controller 87 receives the menu display command, it displays a title input screen for image and an image distribution destination input screen which forms the image (electronic mail) distribution destination.

The user now inputs the title of the image and the image (electronic mail) distribution destination.

When the title is input, the device control unit data receiver 86 or the long-distance control unit data receiver 91 transmits this title via the process control manager 92 to the endoscope information holder 93. The endoscope information holder 93 stores this title in correspondence with the image.

When information relating to the distribution destination of the image is input, the device control unit data receiver 86 or the long-distance control unit data receiver 91 transmits the information relating to the distribution destination as image distribution destination data via the process control manager 92 to the captured image distribution destination data manager 94. The captured image distribution destination data manager 94 stores this information relating to the distribution destination. A character signal is physically stored in the RAM 38 (or the ROM 41).

By such processes, when the menu display command is input to the device control unit 11 or the long-distance control unit 51, a menu for inputting the title of the image and the distribution destination of the electronic mail is displayed, and, when a character signal is input, this character signal is stored as the title of the image and the distribution destination of the electronic mail.

When distributing the image by electronic mail at a desired date and time which have been set, the date and time for distributing the electronic mail are set in the timer control circuit 46.

The timer controller 90 monitors the date and time from the timer control circuit 46, and transmits an interrupt signal to the process control manager 92 at the set date and time. When the process control manager 92 receives the interrupt signal from the timer controller 90, it transmits an image obtain command to the image-capturing processor 89. When image-capturing processor 89 receives the image obtain command, it controls the A/D converter 36 and the compression processor 37 such that the image data from the CCD 31 is compressed and stored in the RAM 38. When storage of the compressed image in the RAM 38 is complete, the image-capturing processor 89 transmits a captured image storage completion notification to the process control manager 92.

When the process control manager 92 receives the captured image storage completion notification, it sends a distribution command relating to the captured image to the image distributor 95. As shown in the flowchart of FIG. 6, when the image distributor 95 receives this distribution command relating to the captured image from the process control manager 92, it creates electronic mail data for the captured image and transmits it via electronic mail.

By such processes, the captured image from the endoscope which was captured by the CCD 31 is transmitted by electronic mail at the desired date and time.

When distributing the captured image by electronic mail in accordance with the external trigger signal, the trigger signal input terminal 48 supplies a digital or analog trigger signal to the external trigger input circuit 47.

The external trigger input unit 88 monitors whether a digital or analog trigger signal has been input from the external trigger input circuit 47, and, when a trigger signal is input, transmits an interrupt signal to the process control manager 92. When the process control manager 92 receives the interrupt signal from the external trigger input unit 88, it transmits a captured image obtain command to the image-capturing processor 89. When the image-capturing processor 89 receives the captured image obtain command, it controls the A/D converter 36 and the compression processor 37 such as to compress the captured image data from the CCD 31 and store it in the RAM 38. When storage of the compressed image in the RAM 38 is completed, the image-capturing processor 89 transmits a captured image storage completion notification to the process control manager 92.

When the process control manager 92 receives the captured image storage completion notification, it sends a distribution command for the captured image to the image distributor 95. As shown in the flowchart of FIG. 6, when the image distributor 95 receives a distribution command for the captured image from the process control manager 92, is creates electronic mail data for the captured image and transmit it by electronic mail.

By such processes, when an external trigger signal is input, the captured image of the endoscope which was captured by the CCD 31 is transmitted by electronic mail to the distribution destination.

Figure 7:
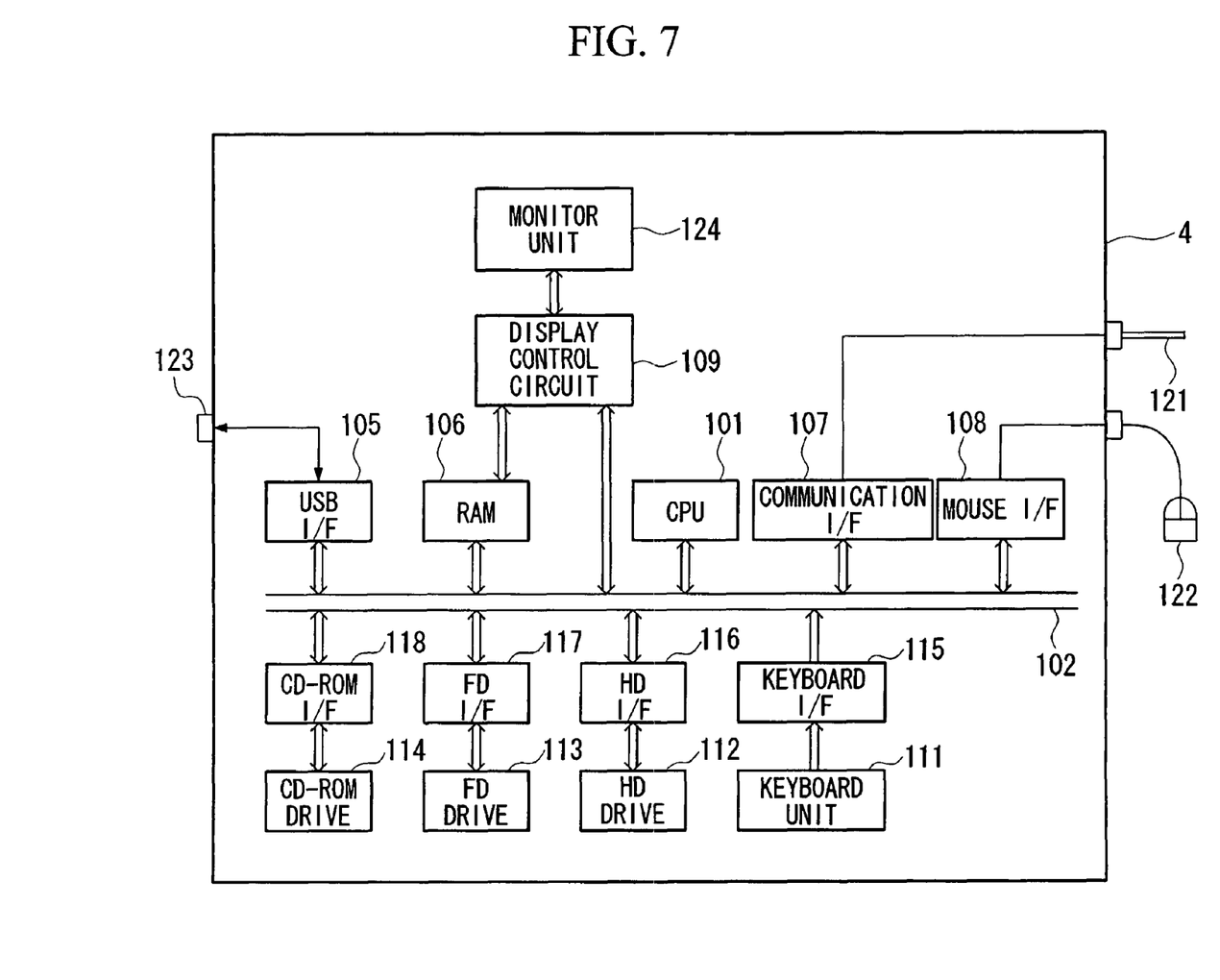
FIG. 7 is a block diagram showing a captured image management computer according to the embodiment of the present invention.

Subsequently, the captured image management computer 4 according to an embodiment of the present invention will be explained. FIG. 7 is a block diagram of the internal configuration of the captured image management computer 4.

A CPU 101 entirely controls the captured image management computer 4, and is connected to an internal bus 102. A USB interface 105, a RAM 106, a communication interface 107, and a mouse interface 108 are connected to the internal bus 102. A display control circuit 109 for controlling a monitor unit 124 is also connected to the internal bus 102.

A keyboard unit 111, a hard disk (abbreviated to HD in FIG. 7) drive 112, a flexible disk (abbreviated to FD) drive 113, and a CD-ROM drive 114 are connected to the internal bus 102 via interfaces 115, 116, 117, and 118 respectively.

A communication line such as a LAN or the internet is connected to the communication interface 107 via a cable 121. A mouse 122 is connected to the mouse interface 108. The USB interface 105 is connected to a USB connector 123.

The CPU 101 operates in compliance with programs of an operation system in the HD drive 112. At least an electronic mail transmission/reception program and an image reproduction program are installed in the HD drive 112. When the electronic mail program is activated, endoscope image data transmitted via the network 6 from the endoscope devices 2a and 2b is received, and this image data is stored in the HD drive 112.

With regard to the mail received from the endoscope devices 2a and 2b, the CPU 101 displays a list of categories consisting of the title of the electronic mail, the date and time when it was received, and its transmission source. Endoscope information such as the date and time when the image was captured, the title of the captured image, the lens type, the correction value of the image-capturing lens, the management number of the endoscope device, captured image correction information, and user information are written in title and/or the text of the electronic mail. For the operator and the manager of the captured image, this avoids a burden of confirming the captured image, conditions, and the like, and then creating data. Simultaneously, this enables an captured image manager who receives the electronic mail to organize the attached image without opening and viewing it, merely by reading the title and/or text, thereby greatly reducing the burden on the operator and the manager.

Figure 8:
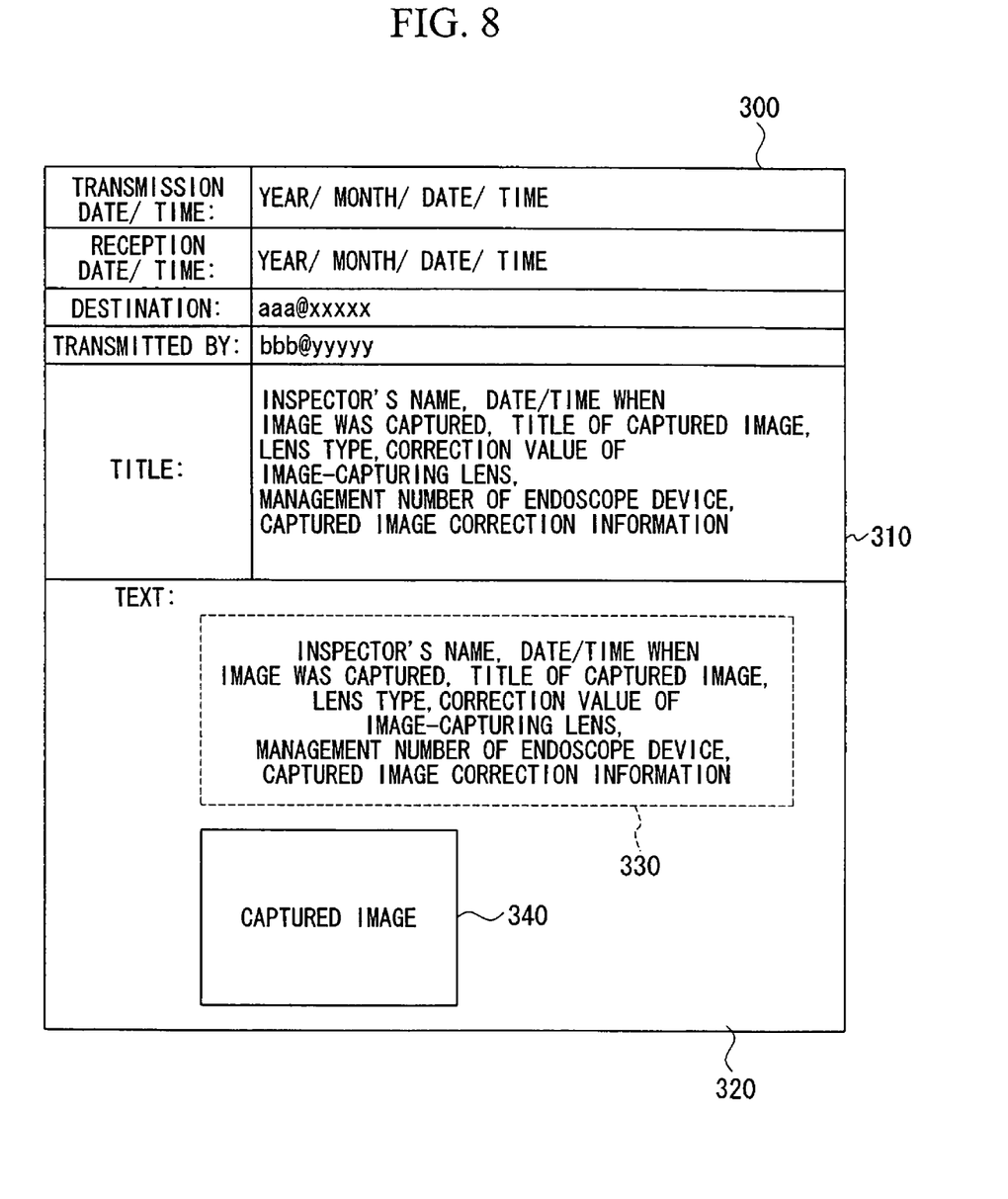
FIG. 8 is a diagram showing one example of an electronic mail created by the embodiment of the present invention.

FIG. 8 shows an example of a configuration of an electronic mail 300 according to this embodiment. The electronic mail 300 shown in FIG. 8 is transmitted from the endoscope devices 2a and 2b of the examination sites 1a and 1b and received by the captured image management computer 4. In FIG. 8, endoscope information is written in a title box 310 of the electronic mail 300. The endoscope information 330 is also written in a text box 320 of the electronic mail 300, and a captured image 340 is attached.

While in the example of FIG. 8, the endoscope information is written in both the title box 310 and the text box 320, it would be acceptable to write it only in one of these. While the name of the inspector is written as user information of the endoscope information, any type of information that enables the inspector to be identified, such as an ID number, can be used as the user information. The positions of the endoscope information 330 and the captured image 340 in the text box 320 can be set at will, as can the description format of the endoscope information.

The present invention is not to be considered as being limited by the embodiment described above, and can be modified and applied in various ways without departing from the scope of the invention.

For example, although the embodiment described above uses electronic mail as the communication system for transmitting the captured image and the endoscope information, a communication system other than electronic mail could be used. One example of a communication system other than electronic mail would be to store the captured image and the endoscope information in a file, and then use a file transfer protocol (FTP) to transfer this file from the endoscope device to the captured image management device.

As described above, in the endoscope control system of the present invention, endoscopes at each inspection site transmit captured images via a predetermined communication system such as electronic mail to a distribution destination, being a captured image computer at a management center which manages the captured images. At the management center, the captured images from the endoscopes arrive via the predetermined communication system such as electronic mail, and are managed. This enables an operator to transmit the images captured by the endoscopes directly to a captured image manager. This eliminates the troublesome labors of removing the recording medium from the endoscope after work ends, connecting it to the computer of the operator, transferring the captured images in the recording medium to the computer of the operator, and transmitting them by electronic mail to the captured image manager. Endoscope information such as the date and time when the image was captured, the title of the captured image, the lens type, the correction value of the image-capturing lens, the management number of the endoscope device, captured image correction information, and user information, is written in the title and/or the text of the electronic mail and transmitted to the captured image manager, thereby eliminating the burden on the operator of creating data while confirming the captured image, conditions, and so on. The captured image manager who receives the electronic mail can organize the attached image merely by reading the title and/or the text, without opening and viewing it, thereby eliminating the burden on the captured image manager. Therefore, the burden on the operator and the captured image manager after inspection can be greatly reduced.

What is claimed is:

1. An endoscope system comprising:

a captured image management device for collectively managing captured images transmitted thereto via a network on an electronic mail communication system;

a data manager for managing an electric mail address of the captured images, the data manager storing the electric mail address;

an endoscope device which has an elongated insertion unit, the insertion unit being freely bendable, the endoscope device reading the electric mail address from the data manager, the endoscope device including an image-capturing unit for capturing an image of an inspection region, and the image-capturing unit provided at a tip of the insertion unit; and a long-distance control unit which is connected to the network for controlling the endoscope device, the long-distance control unit receiving an input of a title of the captured image captured by the image-capturing unit and transmitting the title to the endoscope device;

the endoscope device further including:

a mail creation unit which creates an electronic mail destined for the captured image management device with the captured image captured by the image-capturing unit attached thereto, the electronic mail creation unit writing the title of the captured image in at least one of a title and a text of the electronic mail: and a transmitter for transmitting the created electronic mail via the electronic mail communication system to the captured image management device.

2. The endoscope system according to claim 1, wherein:

the captured image management device collectively manages the captured image transmitted by electronic mail via the network; and the transmitter transmits the created electronic mail to the network.

3. The endoscope system according to claim 2, wherein:

the endoscope device includes an endoscope information storage unit which stores the endoscope information; and the mail creation unit stores the captured image captured by the image-capturing unit together with endoscope information stored in the endoscope information storage unit.

4. The endoscope system according to claim 3, wherein the mail creation unit writes the endoscope information in at least one of the title and the text of the electronic mail.

5. The endoscope system according to claim 1, wherein the endoscope device includes a device control unit, and a distribution controller which distributes the captured image captured by the image-capturing unit to the communication system when a control signal from the device control unit is input.

6. The endoscope system according to claim 1, wherein the endoscope device is connected to the long-distance control unit, and includes a distribution controller which distributes the captured image captured by the image-capturing unit to the communication system when a control signal from the long-distance control unit is input.

7. The endoscope system according to claim 1, wherein the endoscope device includes a timer, and a distribution controller which distributes the captured image captured by the image-capturing unit to the communication system when the timer reaches a desired date and time.

8. The endoscope system according to claim 1, wherein an external trigger signal is supplied to the endoscope device, and the endoscope device includes a distribution controller which distributes the captured image captured by the image-capturing unit to the communication system when the external trigger signal is input.

9. The endoscope system according to claim 1, wherein the endoscope device includes an endoscope information storage unit which stores endoscope information.

10. The endoscope system according to claim 9, wherein the endoscope information includes at least a date and time when the image was captured, the title of the captured image, a correction value of an image-capturing lens, the lens type, a management number of the endoscope device, captured image correction information, and user information.

11. The endoscope system according to claim 1, wherein an electronic mail transmitting/receiving program is installed in the captured image management device and the endoscope device.

12. The endoscope system according to claim 11, wherein the electronic mail transmitting/receiving program encrypts/decrypts electronic mail.

13. The endoscope system according to claim 1, further comprising a memory which stores the captured images, wherein the endoscope device reads the captured images from the memory.

14. The endoscope system according to claim 1, wherein the long-distance control unit transmits to the endoscope device an image record command to record the image captured by the image-capturing unit, and the endoscope device further includes:

an interface unit in which a recording medium is inserted; and an image-capturing processor which stores the image captured by the image-capturing unit to the recording medium inserted in the interface unit based on the image record command received by the endoscope device.

15. The endoscope system according to claim 1, wherein the long-distance control unit transmits to the endoscope device a captured image transmission command to transmit the image captured by the image-capturing unit via the electronic mail communication system, and the endoscope device transmits the created electronic mail based on the captured image transmission command received by the endoscope device.

16. The endoscope system according to claim 1, wherein the long-distance control unit transmits to the endoscope device an image adjustment command to execute adjustment to the image captured by the image-capturing device, the endoscope device further includes:

an image processor which adjusts and processes the image captured by the image-capturing device; and an image adjustment processor which controls the image processor to adjust the image captured by the image-capturing device based on the image adjustment command received by the endoscope device.

17. The endoscope system according to claim 1, wherein the long-distance control unit transmits to the endoscope device an insertion unit drive command to bend the tip of the insertion unit, and the endoscope device further includes an insertion bend controller which bends the tip of the insertion unit based on the insertion unit drive command received by the endoscope device.

18. A method for transmitting an electronic mail comprising:

receiving an input of a title of an image captured by an image-capturing unit provided at a tip of an elongated insertion unit of an endoscope device, via a network:

transmitting the title of the captured image to the endoscope device;

reading endoscope information including the title of the captured image from a holder;

writing the endoscope information in at least one of a title and a text of the electronic mail at the endoscope device;

reading the captured image from a memory;

attaching the captured image to the electronic mail;

reading a distribution destination of the electronic mail from a data manager; and transmitting the electronic mail from the endoscope device to the distribution destination.

* * * * *